(12) United States Patent
Koo et al.

(10) Patent No.: US 8,449,913 B2
(45) Date of Patent: May 28, 2013

(54) METHODS OF ADMINISTERING A DERMATOLOGICAL AGENT TO A SUBJECT

(75) Inventors: John Koo, San Francisco, CA (US);
Jutaro Shudo, San Jose, CA (US);
Sadanobu Shirai, Takamatsu (JP)

(73) Assignees: Teikoku Pharma USA, Inc., San Jose, CA (US); Teikoku Seiyaku Kabushiki Kaisha, Kagawa (JP)

( * ) Notice: Subject to any disclaimer, the term of this patent is extended or adjusted under 35 U.S.C. 154(b) by 120 days.

(21) Appl. No.: 12/767,638

(22) Filed: Apr. 26, 2010

(65) Prior Publication Data

US 2010/0203107 A1     Aug. 12, 2010

Related U.S. Application Data

(62) Division of application No. 10/754,477, filed on Jan. 8, 2004, now Pat. No. 7,887,842.

(60) Provisional application No. 60/445,572, filed on Feb. 7, 2003.

(51) Int. Cl.
*A61K 9/14*     (2006.01)

(52) U.S. Cl.
USPC .......................................... 424/484; 424/485

(58) Field of Classification Search
None
See application file for complete search history.

(56) References Cited

U.S. PATENT DOCUMENTS

| | | | |
|---|---|---|---|
| 3,891,757 A | 6/1975 | Higuchi | ........................ 514/772 |
| 4,009,282 A | 2/1977 | Voorhees | ...................... 514/573 |
| 4,909,244 A | 3/1990 | Quarfoot et al. | |
| 4,917,890 A | 4/1990 | McAnalley | |
| 5,013,769 A | 5/1991 | Murray et al. | .............. 424/78.06 |
| 5,076,265 A | 12/1991 | Wokalek | |
| 5,147,344 A * | 9/1992 | Sachau et al. | .................. 604/368 |
| 5,405,366 A * | 4/1995 | Fox et al. | ......................... 607/50 |
| 5,456,745 A * | 10/1995 | Roreger et al. | ............ 106/140.1 |
| 5,695,777 A | 12/1997 | Donovan et al. | |
| 5,897,880 A | 4/1999 | Drizen et al. | |
| 5,902,827 A | 5/1999 | Pamukcu et al. | .............. 514/530 |

(Continued)

FOREIGN PATENT DOCUMENTS

| | | |
|---|---|---|
| CN | 1243437 A | 2/2000 |
| CN | 1302608 A | 7/2001 |

(Continued)

OTHER PUBLICATIONS

Alopecia Areata, MedicineNet.com; accessed online Jun. 18, 2012.*

(Continued)

*Primary Examiner* — Anand Desai
*Assistant Examiner* — Melissa Mercier
(74) *Attorney, Agent, or Firm* — Bret E. Field; Brian Davy; Bozicevic, Field & Francis, LLP (57) ABSTRACT

Methods for administering a dermatological agent to a subject are provided. In the subject methods an effective amount of a topical formulation of the dermatological agent is topically applied to a host. The topically applied formulation of dermatological agent is then occluded with a hydrogel patch, where a feature of the hydrogel patch is that it lacks a pharmaceutically active agent. Also provided are methods of treating a subject for a disease condition by administering a dermatological agent to the subject. Also provided are kits for use in practicing the subject methods. The subject methods and compositions find use in a variety of different applications.

19 Claims, 3 Drawing Sheets

U.S. PATENT DOCUMENTS

| | | | |
|---|---|---|---|
| 6,147,102 | A | 11/2000 | Borgman |
| 6,348,212 | B2 * | 2/2002 | Hymes et al. ............... 424/449 |
| 6,455,065 | B1 * | 9/2002 | Hymes ............... 424/449 |
| 6,645,520 | B2 | 11/2003 | Hsu et al. ............... 424/449 |
| 7,988,990 | B2 | 8/2011 | Shirai |

FOREIGN PATENT DOCUMENTS

| | | |
|---|---|---|
| DE | 40 06 628 | 3/1990 |
| EP | 0 630 629 A1 | 12/1994 |
| EP | 1 591 111 | 11/2005 |
| GB | 1216908 | 3/1967 |
| JP | 2003188149 | 8/1991 |
| JP | 20011228340 | 8/1999 |
| KR | 1020010096776 A | 11/2001 |
| WO | 9800145 | 1/1998 |
| WO | WO 98/30214 A1 | 7/1998 |
| WO | WO 99/04829 | 2/1999 |
| WO | WO 01/30345 A1 | 5/2001 |
| WO | WO 2004/030696 | 4/2004 |
| WO | 2004/066985 | 8/2004 |

OTHER PUBLICATIONS

Castelijn et al. The epidermal phenotype during initiation of the psoriatic lesion in the symtomless margin of relapsing psoriasis, Dec. 9, 1998, Department of Dermatology, University Hospitol Nijemgen. p. 901-909.

Agren et al., A comparative study of three occlusive dressings in the treatment of full-thickness wounds in pigs, J. Am. Acad. Dermato., 1997, 36:53-58.

Bello et al., Practical treatment of body and open leg wounds of horses with bovine collagen, biosynthetic wound dressing and cyanoacrylate, J. of Equine Veterinary Science, 2002; 22(4), 157-164.

Castelijns et al., The epidermal phenotype during initiation of the psoriatic lesion in the symptomless margin of relapsing psoriasis, J. Am. Acad. Dermatol. 1999; 40:901-909.

Castelijns, F.A.C.M., et al., "Efficacy of Calcipotriol Ointment Applied Under Hydrocolloid Occlusion in Psoriasis." Dermatology (2002); 200: pp. 25-30.

C.P. Glade, et al., "Flow Cytometric Assessment of Clearance and Relapse Characteristics in Psoriasis Vulgaris After Treatment With Weekly Clobetasol Lotion Under Hydrocolloid Occlusion Versus Twice-Daily Clobetasol Ointment." Skin Pharmacol Appl. Skin Physical (2002); 15: pp. 92-99.

Duweb G.A. et al., "Occlusive Versus Nonocclusive Calcipotriol Ointment Treatment for Palmoplantar Psoriasis." Int. J. Tissue React (2001) 23(2): pp. 59-62.

Marsland AM, Griffiths CE ., "Treatments for Chronic Palmoplantar Pustular Psoriasis." Skin Therapy Lett Nov. 6, 2001(12); pp. 3-5.

Mommers, J.M., et al., "Clobetasol Under Hydrocolloid Occlusion in Psoriasis Results in a Complete Block of Proliferation and in a Rebound of Lesions Following Discontinuation." Dermatology 1999; 199: pp. 323-327.

Scher R.K. et al., "Tazarotene 0.1% Gel in the Treatment of Fingernail Psoriasis: A Double-Blind, Randomized, Vehicle-Controlled Study." Cutis Nov. 2001; 68(5): pp. 355-358.

Taylor Ks, et al., "Pituitary-Adrenal Function Following Topical Triamcinolone Acetonide and Occlusion." Arch Dermatology Aug. 1965; 92(2): pp. 174-177.

Van der Vleuten CJ, et al., "Clobetasol-17-Propionate Lotion Under Hydrocolloid Dressing (Duoderm ET) Once Weekly Versus Unoccluded Clobetasol-17-Propionate Ointment Twice Daily in Psoriasis: An Immunohistocheniical Study on Remission and Relapse." Archives of Dermatological Research Jul.-Aug. 1999; pp. 291(7-8): 390-395.

Volden G. et al., "Remission and Relapse of Chronic Plaque Psoriasis Treated Once a Week With Clobetasol Propionate Occluded With a Hydrocolloid Dressing Versus Twice Daily Treatment With Clobetasol Propionate Alone." Journal of Dermatology Treat Sep. 2001:12(3); pp. 141-144.

Japanese Patent Application No. 2006-502835, Official Action Summary, dated Nov. 27, 2012, 3 pages.

* cited by examiner

METHODS OF ADMINISTERING A DERMATOLOGICAL AGENT TO A SUBJECT

CROSS-REFERENCE TO RELATED APPLICATIONS

Pursuant to 35 U.S.C. §119 (e), this application claims priority to the filing date of the U.S. Provisional Patent Application Ser. No. 60/445,572 filed Feb. 7, 2003; the disclosure of which is herein incorporated by reference.

INTRODUCTION

1. Field of the Invention

The field of this invention is pharmaceuticals, particularly topical pharmaceutical preparations.

2. Background of the Invention

Skin conditions or dermatological disorders afflict millions of people each day. These skin conditions may be acute (lasting for just a few minutes to a few hours) or chronic conditions that may plague an individual for days, months, years or even a lifetime. A multitude of different dermatological conditions exist and may be fungal, bacterial, or viral based, or may be a non-infective, immunological response such as an inflammatory response with or without an allergic component, or may be idiopathic. Accordingly, symptoms may vary and may range from mild itching, redness and swelling to severe pustules and open sores and even in certain instances may lead to debilitating manifestations such as disabling ulcerations. Regardless of the cause or particular symptoms, dermatological disorders may substantially affect the quality of an individual's life.

Topical dermatological agents have been employed for decades to treat or otherwise alleviate the symptoms of a variety of dermatological conditions. However, a number of these topical dermatological agents require a prolonged treatment regime of a particular dosage in order to be effective at treating a dermatological disorder. One problem that arises with the use of many of these topical dermatological agents is that they may require application over an extended period of time to be effective at treating a particular disorder, where such extended periods of time may be required due to the efficiency of the agent employed. Such extended treatment periods may be inconvenient and disruptive to a subject life.

The amount of time a particular topical dermatological agent may be used on an individual may be limited by side effects or potential side effects that may develop over such extended periods of time of use. The occurrence of side effects depends on the dose, type of topical dermatological agent and length of treatment and, of course, some side effects are more serious than others. While some side effects may be reversible, others are not and thus care must be taken to so that these types of side effects are avoided. Common side effects of some topical dermatological agents used to treat certain disease disorders include thinning of the skin, local burning, itching, irritation, dryness, redness of the skin, acne, striae or stretch marks, dilation of blood vessels in the skin, tachyphylaxis, skin color (pigmentation) changes, easy bruising, and the like.

For example, psoriasis affects approximately 2-3% of the world's population and about 7 million people in the U.S. Psoriasis is a chronic, inflammatory, hyperproliferative disease of the skin characterized by well-demarcated, erythematous, scaly plaques. Psoriasis may consist of one or two lesions or may be a widespread dermatosis with disabling arthritis or exfoliation. Although the exact pathogenesis of psoriasis remains undefined, there are several therapeutic options. For example, monoclonal antibodies have been employed in attempts to combat psoriasis, however this treatment option is used primarily to treat generalized psoriasis as opposed to localized psoriasis. Since most sufferers of psoriasis have only localized psoriasis, the mainstay of treatment remains the use of topical agents.

Topical steroids, such as triamcinolone, have been used in the treatment of psoriasis for years. While topical steroids are often effective in the treatment of psoriasis, their use may be associated with adverse side effects such as those described above as well as skin atrophy or systemic effects such as HPA-axis suppression if used extensively. Furthermore, tachyphylaxis may result from the use of the topical steroid. In clinical practice, while most localized lesions respond to topical corticosteroids, some lesions remain recalcitrant to even the strongest "Class I" topical steroids such as clobetasol. The use of Class I super potent topical steroids is typically limited to only two weeks because of potential side effects.

Accordingly, there remains a need to increase the effectiveness and/or efficiency of a dermatological agent, e.g., to shorten the otherwise extended treatment period (increase efficiency), increase the effectiveness of an agent, etc. A variety of protocols have been developed to try to increase the efficiency and/or effectiveness of a topical agent, although thus far such protocols have met with limited success. For example, dermatological agents have been provided in a variety of topical formulations such as creams, lotions, gels and the like in attempts to increase the delivery efficiency. However, while enabling direct, localized application of the dermatological agent to a skin surface, these topical formulations have not provided a complete solution as typically only partial improvement results even with an optimal formulation, e.g., oftentimes recalcitrant skin lesions remain, and/or treatment times have not been appreciably shortened.

Attempts to enhance the efficacy of the dermatological agent by covering these topical formulations with plastic wrap such as Saranwrap® once the formulations have been applied has also been tried and has met with some success in enhancing the efficacy of the dermatological agent. However, this method is messy, uncomfortable and inconvenient, for example the plastic wrap is difficult to keep in place, especially when positioned on an elbow, knee, shin, etc. In attempts to try to maintain the plastic wrap in position at an application site, adhesive tapes have been employed. However, many people have allergies to such adhesive tapes. Furthermore, a site may become irritated by the use of adhesive tape causing tape burns. Certain skin diseases such as psoriases tend to develop at the site of the superficial skin trauma caused by the tape.

Accordingly, there continues to be an interest in the development of new methods of topically administering a dermatological agent to a subject. Of particular interest is the development of such methods that are cost effective, easy to use, and which are effective as well as efficient at administering or enhancing the dermatological agent to the subject.

RELEVANT LITERATURE

U.S. Patents of interest include: U.S. Pat. Nos. 5,120,544; 5,160,328; 5,270,358; 5,423,737; 5,476,443; 5,489,262; 5,501,661; 5,827,529; 6,039,940; 6,096,333; 6,214,374; 6,296,869; 6,348,212; 6,455,065. Also of interest are WO 02/078757 and WO 02/078756.

SUMMARY OF THE INVENTION

Methods for administering a dermatological agent to a subject are provided. In the subject methods an effective amount of a topical formulation of the dermatological agent is topically applied to a host. The topically applied formulation of dermatological agent is then occluded with a hydrogel patch, where a feature of the hydrogel patch is that it lacks a pharmaceutically active agent. Also provided are methods of treating a subject for a disease condition by administering a dermatological agent to the subject. Also provided are kits for use in practicing the subject methods. The subject methods and compositions find use in a variety of different applications.

DETAILED DESCRIPTION OF THE INVENTION

Methods for administering a dermatological agent to a subject are provided. In the subject methods an effective amount of a topical formulation of the dermatological agent is topically applied to a host. The topically applied formulation of dermatological agent is then occluded with a hydrogel patch, where a feature of the hydrogel patch is that it lacks a pharmaceutically active agent. Also provided are methods of treating a subject for a disease condition by administering a dermatological agent to the subject. Also provided are kits for use in practicing the subject methods. The subject methods and compositions find use in a variety of different applications.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges and is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

The figures shown herein are not necessarily drawn to scale, with some components and features being exaggerated for clarity.

As summarized above, the present invention provides methods and compositions for administering a dermatological agent to a host. In further describing the subject inventions, the methods and compositions are described first in greater detail, followed by a review of representative applications in which the methods and compositions may be employed.

Methods and Compositions

In accordance with the subject invention, a topical formulation of a dermatological agent is administered to a subject using a hydrogel patch composition to occlude the dermatological agent. A feature of the subject hydrogel patch compositions are that they lack a pharmaceutically active agent, i.e., they are "blank" hydrogel patches, as will be described in greater detail below. Thus, in practicing the subject invention, a topical formulation of a dermatological agent is topically applied to an application site on a subject. Once topically applied, the topical formulation of a dermatological agent is then occluded by a blank hydrogel patch composition. The occluded topical formulation is maintained for a sufficient amount of time to administer an effective amount of the dermatological agent to the subject.

In accordance with the subject invention, an improved protocol for administering a dermatological agent to a subject is provided. By "improved" it is meant that the delivery of the agent through the skin is improved as compared to the topical administration of the dermatological agent without occlusion according to the subject invention, i.e., as compared to a control. For example, the efficiency and/or effectiveness of the dermatological agent may be increased or enhanced according to the subject invention, e.g., as measured by one or more of the following: an improvement in the morphology of a skin lesion being treated, an improvement in pruritis, an improvement in treatment time, etc., as compared to a control. The magnitude of improvement may vary depending on the particular dermatological agent, condition being treated, etc. In certain embodiments, the magnitude of improvement may be at least about 2-fold, e.g., at least about 5-, 10-, 15-, 20-, 25-, 50-, 75-fold or more.

Any appropriate dermatological agent may be administered by the subject methods. Typically, the dermatological agent has anti-inflammatory and/or anti-proliferative and/or immunomodulatory properties. It shall be understood that the dermatological agents described herein should not be considered to be limiting in any manner in that many other dermatological agents not referenced herein may be utilized to practice the subject invention, including dermatological agents yet to be discovered.

As mentioned above, the dermatological agent that is applied to treat the particular disorder is present in a topical formulation. By "topical formulation" it is meant that the dermatological agent is present in a form that is capable of application to the surface of the skin and is able to be absorbed through the skin. Such topical formulations of dermatological agents are typically in the form of a cream, lotion, ointment, gel, solution, foam, powder, and the like. The concentration of the dermatological agent will depend on the particular agent, the particular disease disorder, the host, the site of application, and the like.

Various classes of dermatological agents may be utilized in accordance with the subject invention. As such, any dermatological agent may be employed that has desirable therapeutic properties for the particular skin disorder being treated. In certain embodiments, the topical formulation of a dermatological agent applied to the surface of the skin is a steroid. Thus, in accordance with the subject invention, any class of steroid may be employed in accordance with the subject invention. That is, Class I steroids (very potent steroids), Class II steroids (potent steroids), Class III steroids (moderately potent steroids) and Class IV steroids (relatively mild steroids), etc., may be used with the subject invention, as long as they are in a form for topical application. A variety of steroids are known in the art for treatment of disorders affecting the skin and include, but are not limited to: triamcinolone, triamcinolone acetonide, clobetasol, clobetasol propionate, clobetasone butyrate, desonide, alclometasone, flurandrenolide, desoximetasone, betamethasone, loteprednol, fluorometholone, difluprednate, mometasone furoate, diflorasone diacetate, diflucortolone valerate, fluocinonide, amcinonide, halcinonide, fluocinolone acetonide, flumetasone pivalate, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone, chloroprednisone, chlorprednisone acetate, clocortelone, clescinolone, dichlorisone, diflurprednate, flucloronide, flunisolide, fluorometholone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone. A combination or mixture of one or more of the above dermatological agents may be employed.

However, the subject invention is not limited to dermatological agents that include steroids. Accordingly, in certain embodiments, the dermatological agent applied to the surface of the skin is not a steroid. For example, the dermatological agent may be an anti-bacterial agent such as mupirocin (e.g., Bactroban®), etc., an anti-viral agent such as topical acyclovir (e.g., Zovirax®), etc., an anti-fungal agent such as nystatin, miconazole, amphotericin, econazole, etc., an anti-acne agent such as benzoyl peroxide, a vitamin A derivative, a vitamin D derivative, a vitamin E derivative, etc. Other non-steroidal agents are known in the art and include, but are not limited to: calcipotriol (e.g., Dovonex®), pimecrolimus (e.g., Elidel®), tacrolimus (e.g., Protopic®), tazarotene (e.g., Tazorac®), coal tar, anthralin (e.g., Psoriatec™), salicylic acid, sulfur products such as colloidal sulfur, etc. A combination or mixture of one or more of the above dermatological agents may be employed, e.g., a combination of coal tar, salicylic acid and colloidal sulfur (e.g., MG217™). In certain embodiments, a combination or mixture of one or more non-steroidal agents may be used with one or more steroidal agents.

In accordance with the subject invention, once the appropriate topical formulation of dermatological agent is selected, an effective or optimal amount of the topical formulation is applied to a skin surface. As will be apparent to those of skill in the art, the effective or optimal amount will vary depending on the particular dermatological agent employed, the particular disease state being treated, etc. The topical formulation may be applied to any convenient topical site. Topical sites of interest include, but are not limited to: arms, legs, face, neck, torso, etc. Application may be accomplished in any convenient manner and may be dictated at least in part by the form of the topical formulation, i.e., whether the topical formulation is present as a cream, lotion, ointment, gel, solution, foam, powder, etc., the container holding the formulation, etc. For example, the topical formulation may be sprayed onto a skin surface, rolled-onto a skin surface, or a subject may apply the topical formulation using a swab, finger, and the like. Other protocols for applying a topical formulation are known to those of skill in the art and may be employed in accordance with the subject methods.

The amount of surface area upon which the topical formulation is applied may vary depending on the particular disease condition, the particular dermatological agent employed, the application site, etc. The surface area that is covered by the topical formulation must be sufficient to provide for the desired amount of agent administration, and in many embodiments ranges from about 1 to about 1000 $cm^2$ or more, e.g., in certain embodiments ranges from about 10 to about 300 $cm^2$, e.g., from about 20 to about 200 $cm^2$, e.g., about 130 $cm^2$ to about 150 $cm^2$. In certain embodiments, the surface area is sufficient to cover the entire truck of a subject. Accordingly, the surface area may range from about 1000 $cm^2$ to about 5000 $cm^2$ or more, where in certain embodiments the surface upon which the topical formulation is applied may be about 1 m by about 1 m. In practicing the subject methods, a topical formulation may be applied a single time or a plurality of times over a given time period, e.g., the course of the disease condition being treated, where the dosing schedule may be daily, weekly, biweekly, monthly, etc. For example, certain topical formulations may be applied two or more times a day.

A feature of the subject invention is that, following the application of the topical formulation of a dermatological agent to a skin surface, i.e., to an application site, the topically applied topical formulation of dermatological agent is occluded with a hydrogel patch composition. Hydrogels are broadly defined herein as aqueous compositions capable of absorbing water and maintaining a gel-like state. It is to be understood that a hydrogel is not a hydrocolloid, such as a hydrocolloid having the brandname of Duoderm® available from Convatec, Woerden, The Netherlands. Generally, hydrocolloids serve to facilitate removal or absorption of bodily fluids or exudates from skin, e.g., water or other exudates from a wound, whereas the subject hydrogel patches facilitates the delivery or administration into the skin. Moreover, due to the relatively large water content of the subject hydrogel patch compositions relative to hydrocolloids, the subject hydrogel patch compositions are better tolerated by the skin than hydrocolloids, e.g., the subject hydrogel patch compositions may remain in contact with skin for longer periods of time as compared to hydrocolloids.

In certain embodiments, a subject hydrogel patch composition may be employed without a topically applied dermatological agent to treat a subject for a dermatological disorder. In other words, a hydrogel patch composition according to the subject invention may be positioned over a skin surface to treat a dermatological disorder, where a topically applied topical formulation of a dermatological agent has not been immediately applied to the skin surface being covered by a subject hydrogel patch composition.

A feature of the hydrogel patch compositions of the present invention is that they are advantageously inherently adhesive, i.e., are self adhesive, and thus are capable of remaining in a fixed location on a skin surface without the use of ancillary adhesives such as adhesive tape or the like which may cause allergic or other traumatic responses in certain individuals, as described above. While the subject hydrogel patch compositions are inherently adhesive to a skin surface, they are advantageously sufficiently cohesive so as to be easily removable from the skin surface. In contrast, hydrocolloids are not inherently adhesive, i.e., are not self adhesive, and thus require an additional or ancillary adhesive in order to remain affixed to a surface of the skin. As such, the hydrogel patches of the subject compositions are adhesive-free, in contrast to the hydrocolloid topical patch preparations that include an adhesive element, e.g., an adhesive tape covering.

Figure 1:
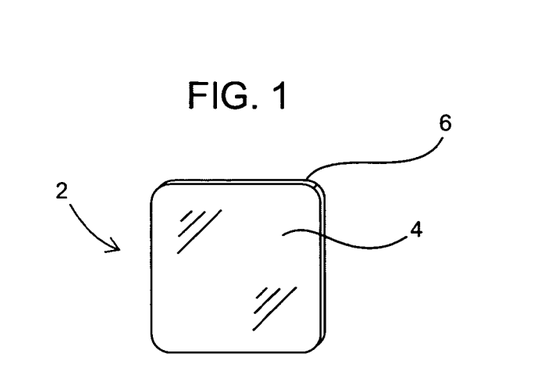
FIG. 1 shows an exemplary embodiment of a hydrogel patch composition device according to the subject methods.

An exemplary embodiment of a subject hydrogel patch composition is shown in FIG. 1 and includes a hydrogel patch composition 4 and an optional support 6 on which the hydrogel patch composition is positioned, collectively referred to in FIG. 1 as element "2". In this particular embodiment, the hydrogel patch composition is rectangular, however this shape is not intended to limit the invention as other shapes are possible as well such as circular, square, triangular, etc., or may be a complex or irregular shape.

A feature of the subject hydrogel patch compositions employed in the subject methods is that the subject hydrogel patch compositions do not include, or rather is void of, a pharmaceutically active agent, as mentioned above. As such, the hydrogel patch compositions of the subject invention may be correctly characterized as "blank" hydrogel patch compositions. In this regard, any pharmaceutically active agent employed in the subject methods is a separate component from the subject hydrogel patch compositions.

In general, the subject hydrogel patch compositions are made up of a water-soluble high molecular weight substance, e.g., a water-soluble polymer gel, water and a water retaining agent. Water-soluble high molecular weight substances of interest include water-soluble polymers, where polymers of interest include, but are not limited to: gelatin, starch, agar, mannan, alginic acid, polyacrylic acid, polyacrylate, dextrin, methylcellulose, sodium methylcellulose, hydroxypropylcellulose, sodium carboxymethylcellulose, cellulose gum, carboxyvinyl polymer, polyvinyl alcohol, polyvinylpyrrolidone, Arabia gum, acacia, tragacanth gum, karaya gum, and starch acrylate copolymer or other starch sodium acrylate graft copolymers. Metallic salts of these, as well as the products of cross-linking these by means of organic or inorganic-cross-linking agents, are also of interest. Specifically, cross-linking agents are typically included in the subject hydrogel patch compositions, where exemplary cross linking agents include, but are not limited to: dried aluminum hydroxy gel, dihydroxy aluminum acetate, magnesium aluminometasilicate, aluminum hydroxide, magnesium metasilicate aluminate, synthetic aluminum silicate, calcium hydroxide, aluminum ammonium sulfate, and calcium chloride. These water-soluble polymers can be used to bring out the properties and characteristics of the other starting materials used in the hydrogel patch composition, and in practice can be used alone or in combinations of 2 or more. The amount of water soluble high molecular weight substance(s) present in the adhesive gel base generally ranges from about 0.5 to about 20% (w/w), usually from about 2 to 15% (w/w) and the amount of cross-linking agent present generally ranges from about 0.01 to about 2% (w/w), usually from about 0.02 to about 1.5% (w/w) and more usually from about 0.03 to about 1% (w/w).

While any convenient water may be employed as the water component, of interest are distilled water or ion-exchange water or the like, which is preferred in many embodiments of the subject invention. The amount of water present in the hydrogel patch composition is sufficient to impart the desired physical properties to the hydrogel patch composition. The amount of water will vary depending on the particular high molecular weight substance(s) employed, where typically the amount of water in the hydrogel patch composition is at least about 25% water by weight, and more usually at least about 30% water (w/w). For example, typically the amount of water ranges from about 25% to about 90%, usually from about 20% to about 80%, where in certain embodiments the amount of water ranges from about 30% to about 50%.

The water-retaining agent or water-holding agent of the subject hydrogel patch compositions is any agent that is capable of at least diminishing the volatilization of water contained in the hydrogel patch composition base so that the water content in the hydrogel patch composition base is maintained at least a substantially constant, if not constant, level during storage and use of the hydrogel patch composition. One or more water-retaining agents may be employed in the subject compositions, where the amount of water-retaining agent present in the adhesive gel base generally ranges from about 1 to about 40%, usually from about 3 to about 30% by weight. Examples of suitable water-retaining or water-holding agents include, but are not limited to: 1 or more types of polyvalent or polyhydric or sugars or alcohols, such as glycerin, sorbitol, propylene glycol, diethylene glycol, 1,3-butylene glycol, and ethylene glycol, and the like.

In addition to the aforementioned ingredients, various additives that are used in ordinary topical water-soluble patch preparations may also be suitably compounded as needed, including inorganic substances such as kaolin, bentonite, and titanium dioxide; preservatives such as paraben; anionic, cationic, and nonionic surfactants; metallic aluminum crosslinking agents such as aluminum chloride, dried aluminum hydroxide gel, and dihydroxyaluminum aminoacetate; oils such as jojoba oil and castor oil; chelating agents such as EDTA; pH regulators such as malic acid, tartaric acid, and diisopropanolamine; alcohols such as ethanol; moisture retaining agents such as hyaluronic acid, aloe extract, and urea; and other perfumes and coloring agents.

The pH of the hydrogel patch composition typically is one that lies in a physiologically acceptable range, where the pH typically ranges from about 3.0 to 8.0 and more typically ranges from about 4.0 to 7.0.

In certain embodiments, the hydrogel patch composition is present on a support or backing. The support is generally made of a flexible material which is capable of fitting in the movement of the human body and includes, for example, various non-woven fabrics, woven fabrics, spandex, flannel, or a laminate of these materials with polyethylene film, polyethylene glycol terephthalate film, polyvinyl chloride film, ethylene-vinyl acetate copolymer film, polyurethane film, and the like. The support may be porous or non-porous, but is typically non-porous or impermeable to the hydrogel composition, dermatological agent employed and fluids, e.g., any fluids exuded from the application site. Such impermeability of the backing increases the effectiveness an efficiency of the hydrogel patch composition. For example, the impermeability of the dermatological agent employed serves to enhance or increase the penetration of the dermatological agent into the skin. By "flexible" it is meant that the support may be substantially bent or folded without breaking, tearing, ripping, etc. The length and width dimensions of the support are typically substantially commensurate, including exactly commensurate, with the length and width dimensions of the hydrogel patch composition with which it is associated. The support layer typically has a thickness ranging from about 10 µm to about 1000 µm, but may be less than 10 µm and/or greater than 1000 µm in certain embodiments.

In addition to the hydrogel patch composition and the optional support layer, the subject patches may also include a release film (not shown) on the surface of the hydrogel composition layer opposite the backing that provides for protection of the hydrogel composition layer from the environment. The release film may be any convenient material, where representative release films include polyesters, such as PET or PP, and the like.

Any convenient hydrogel patch compositions may be adapted and employed for use with the subject invention. Representative hydrogel patch compositions that may be adapted for use with the subject invention include, but are not limited to those described in PCT International Publication Nos.: WO 02/078757 and WO 02/078756 and U.S. Pat. Nos. 5,120,544; 5,160,328; 5,270,358; 5,423,737; 5,476,443; 5,489,262; 5,501,661; 5,827,529; 6,039,940; 6,096,333; 6,214,374; 6,296,869; 6,348,212; 6,455,065; the disclosures of which are herein incorporated by reference.

The hydrogel patch composition may be fabricated using any convenient protocol. One convenient protocol for fabrication of the subject patches includes preparing a hydrogel patch composition paste through the uniform mixing of the aforementioned ingredients and then coating the paste onto the support, followed by cutting of the resultant product to the specified size to obtain the desired hydrogel patch composition. The shape of the patch may vary, where representative shapes include square, rectangle, oval, circle, triangular, etc. The size of the patch may also vary, where in many embodiments the size ranges from about 1 to about 1000 $cm^2$ or more, e.g., in certain embodiments ranges from about 10 to about 300 $cm^2$, e.g., from about 20 to about 200 $cm^2$, e.g., about 130 $cm^2$ to about 150 $cm^2$. In certain embodiments, the surface area is sufficient to cover the entire truck of a subject. Accordingly, the surface area may range from about 1000 $cm^2$ to about 5000 $cm^2$ or more, where in certain embodiments the dimensions of a subject hydrogel patch may be about 1 m by about 1 m. For a more detailed description of the fabrication protocol, see for example U.S. Pat. No. 5,827,529, the disclosure of which is herein incorporated by reference. It should be noted that the above manufacturing protocol is merely representative. Any convenient protocol that is capable of producing the subject hydrogel patch compositions, as described above, may be employed.

Accordingly, to occlude the topically applied topical formulation with a hydrogel patch composition, the hydrogel patch composition is first removed from any packaging that may be present, and then the protective layer, if present, is removed from the patch, thereby exposing the hydrogel patch composition. The hydrogel patch composition is then positioned over the topically applied topical formulation to occlude the topically applied formulation. As mentioned above, the hydrogel patch compositions are self-adhesive, i.e., inherently adhesive, and thus may be fixed in a position over the topically applied topical formulation, i.e., removably bonded to the skin surface, without the use of additional adhesives or other means to hold the patch in place over the formulation. As noted above, in certain embodiments a subject hydrogel patch composition is positioned over a skin surface that does not have a topically applied topical formulation immediately applied thereto.

The topically applied topical formulation is occluded by the hydrogel patch for a period of time sufficient to deliver an effective or therapeutic amount of the dermatological agent to the patient, i.e., through the skin. The particular period of time during which the topical formulation is maintained at the application site depends on a variety of factors such as, but not limited to, the nature of the disease, the dermatological agent employed and the subject, e.g., their sensitivity to the dermatological agent, but is generally at least about 30 seconds and in certain embodiments the period of time may range from about a few hours to about a few days or more, e.g., about one or more days, e.g., about a week or more. In many embodiments, the period of time required to deliver the desired amount of agent is relatively short, generally about 1 or two hours or more, e.g., an hour to about 12 hours, e.g., one hour to about 5-6 hours. In certain embodiments, the period of time required to deliver the desired amount of agent is relatively long, generally at least about 4-5 hours to about 10 hours to about 24 hours or more such as a week or more. Usually the period of time ranges from at least about a few hours to about a week, and usually at least about a few hours to a few days, where a few days may be less than or equal to about seven days. In certain embodiments, the period of time may be as long as about a week or more. These time periods may be total treatment time periods, i.e., the total amount of time a particular area of skin is treated according to the subject methods, or may be a period of time of a first treatment and/or any successive treatments at a particular application site, such that additional treatments according to the subject methods may be performed following a first treatment at a particular application site, e.g., immediately thereafter or after a period of time has passed. Successive treatments may include application of an effective amount of the same topical formulation of dermatological agent used in a previous application, an effective amount of a different dosage of the same dermatological agent used in a previous application, an effective amount of the same dermatological agent present in a different topical formulation (e.g., a cream instead of an ointment), or may include application of an effective amount of a different dermatological agent from that used in a previous application.

Accordingly, in certain embodiments immediately or after a sufficient period of time has elapsed, the subject methods may be repeated one or more times so that an additional dermatological agent (which may be the same or a different agent than used previously) may be applied to an application site and occluded with the same hydrogel patch used previously or different hydrogel patch. The amount of time a hydrogel patch composition may be replaced, for example during the course of a day may range from about 1 time to about two times, and in certain embodiments a subject hydrogel patch may be replaced more than two times in a day. In certain embodiments, for example in the treatment of psoriasis, the hydrogel patch composition and an additional application of topical formulation may be replaced about two times a day.

Once a sufficient amount of time has elapsed, the hydrogel patch composition is removed from the application site. The nature of the hydrogel composition enables it to be easily and non-traumatically removed from the application site by simply peeling the hydrogel patch away from the site. Upon removal, the hydrogel patch composition is removed intact, i.e., the hydrogel patch composition does not leave debris at the site.

Figures 2A, 2B, 2C:
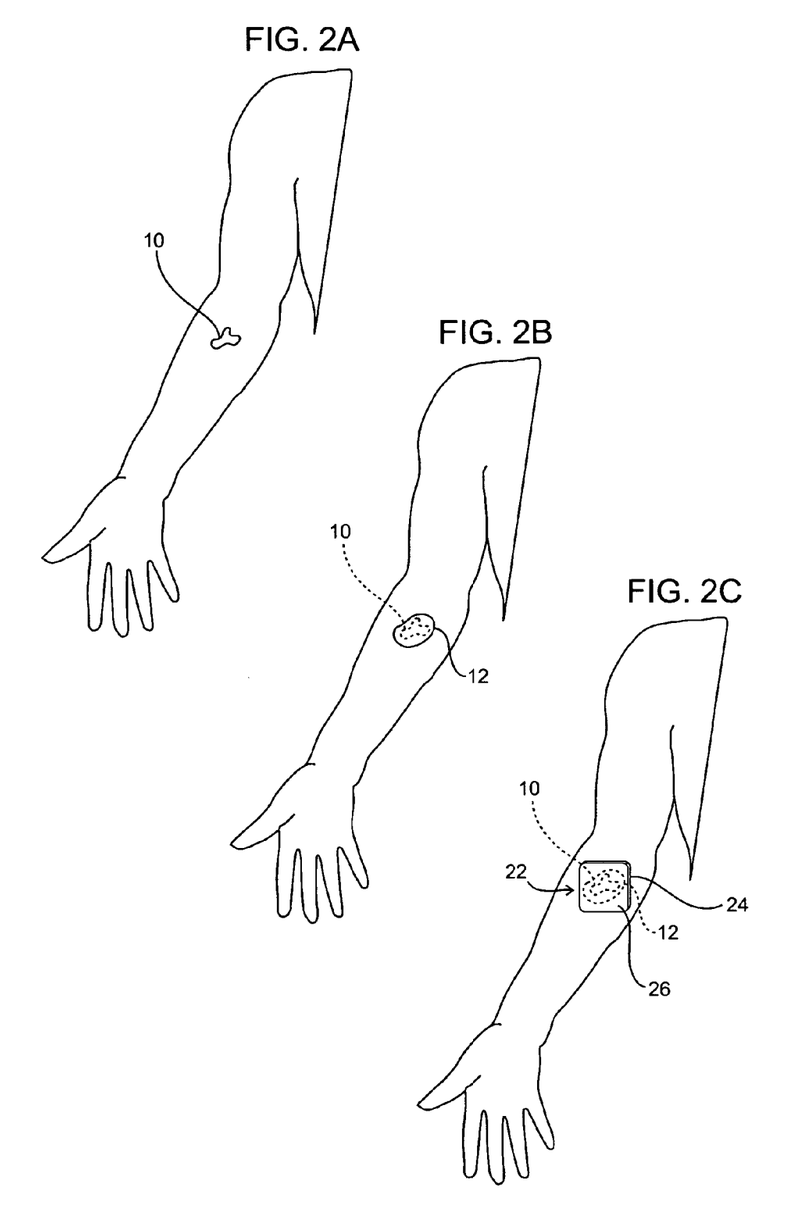
FIGS. 2A-2C illustrate exemplary steps for administering a topical formulation of a dermatological agent to a host in accordance with the subject invention.

FIGS. 2A-2C illustrate an exemplary embodiment of steps for administering a topical formulation of a dermatological agent to an application site according to the subject methods. As shown in FIG. 2A, a skin surface having an application site 10 is present about an elbow of a human host having a disease condition such as a dermatological condition in need of treatment. In accordance with the subject invention, an effective amount of a topical formulation of a dermatological agent 12 is topically applied to the application site, as shown in FIG. 2B. In this particular example, the topical formulation is applied over the entire application site, but this need not be the case in all instances.

As shown in FIG. 2C, once the topical formulation 12 is applied to the application site 10, it is occluded with a hydrogel patch composition 24 to form an occluded topical formulation of dermatological agent. In this particular example, hydrogel patch composition 24 is associated with a support or backing 26, such that a hydrogel patch composition device 22 is provided that includes the hydrogel patch composition 24 and the support 26. The occluded topical formulation of dermatological agent is maintained for a period of time sufficient to treat the host for the disease condition.

After a sufficient amount of time has elapsed, the hydrogel patch composition device 22 is removed from the application site 10. In certain embodiments, at some point after removal of the hydrogel patch composition device 22 from the application site, the above described methods are repeated one or more times such that a second, third, fourth, etc., application of an effective amount of the topical formulation 12 may be applied to application site 10 and occluded with a hydrogel patch composition for a sufficient amount of time. In certain other embodiments, the hydrogel patch composition may be replaced with another hydrogel patch composition without another application of a topical formulation.

Kits

Also provided are kits, where the subject kits at least include one or more hydrogel patch compositions and a topical formulation of a dermatological agent, as described above. The hydrogel patch composition present in the subject kits may be present on a support or backing, e.g., a non-porous support, as described above. In certain embodiments of the subject kits, more than one subject hydrogel patch composition is provided. In such embodiments having more than one hydrogel patch composition, a large number of hydrogel patch compositions may be sealed together within a single packaging. However, typically each hydrogel patch composition present in the kit is sealed in an individual package so that one hydrogel patch composition may be removed from its packaging and used while the packaging of any other hydrogel patch compositions of the kit remains intact or unbreached.

Figure 3:
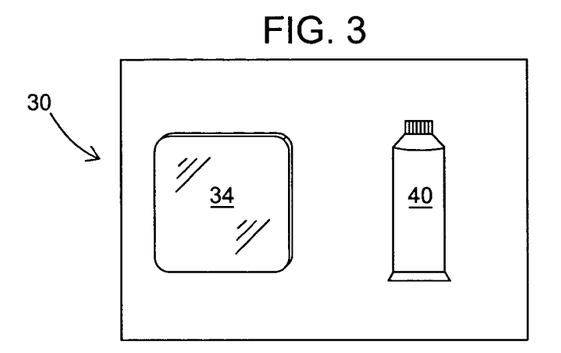
FIG. 3 shows an exemplary embodiment of a subject kit having a single hydrogel patch composition and a single dosage amount of a topical formulation of a dermatological agent.

As mentioned above, the subject kits also include a topical formulation of a dermatological agent. The dosage amount of formulation provided in a kit may be sufficient for a single application or for multiple applications. Accordingly, in certain embodiments of the subject kits a single dosage amount of a topical formulation of a dermatological agent is present in a kit. For example, a kit may include a single hydrogel patch composition and a single dosage amount of a topical formulation of a dermatological agent. FIG. 3 shows an exemplary embodiment of a subject kit 30 (front view) that includes a single hydrogel patch composition 34 and a single dosage amount of a topical formulation of a dermatological agent 40.

Figure 4:
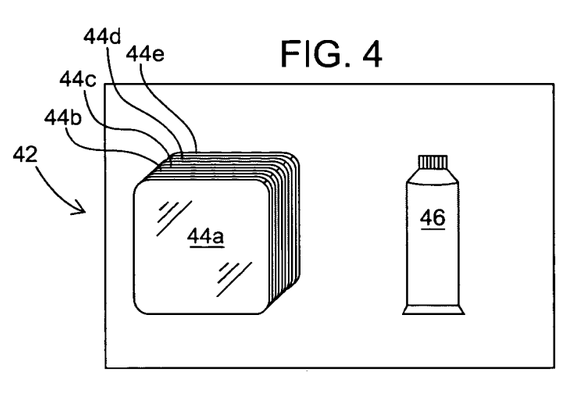
FIG. 4 shows an exemplary embodiment of a subject kit having a plurality of hydrogel patch compositions and a single container having multiple dosage amounts of a topical formulation of a dermatological agent.

In certain other embodiments, multiple dosage amounts of a topical formulation of a dermatological agent may be present in a kit. For example, a kit may include a plurality of hydrogel patch compositions and multiple dosage amounts of a topical formulation of a dermatological agent. In those embodiments having multiple dosage amounts of a topical formulation of a dermatological agent, such may be packaged in a single container, e.g., a single tube, bottle, vial, and the like, or one or more dosage amounts may be individually packaged such that certain kits may have more than one container of a topical formulation of a dermatological agent. FIG. 4 shows an exemplary embodiment of a subject kit 420 (front view) that includes a plurality of hydrogel patch compositions 44a-44e and multiple doses of a topical formulation of a dermatological agent 44. While kit 42 is shown having five hydrogel patch compositions, it shall be understood that fewer or more hydrogel patch compositions may be included in a kit.

Figure 5:
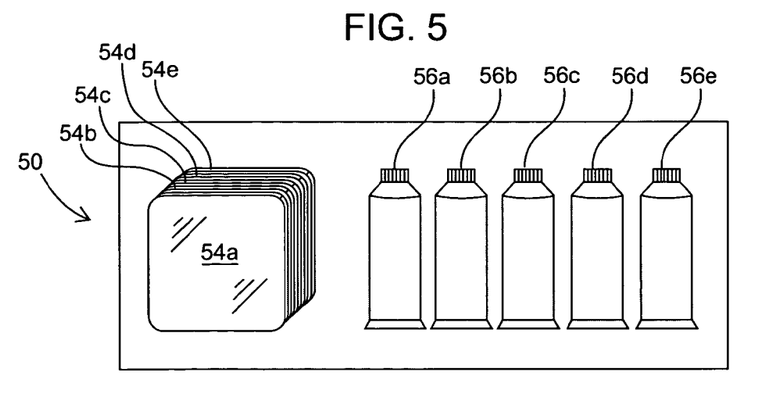
FIG. 5 shows an exemplary embodiment of a subject kit having a plurality of hydrogel patch compositions and a plurality of containers of a topical formulation of a dermatological agent.

As mentioned above, in certain embodiments, more than one container of a topical formulation of a dermatological agent is provided in a kit. FIG. 5 shows an exemplary embodiment of a subject kit 50 that includes a plurality of hydrogel patch compositions 54a-54e and multiple containers 56a-56e of a topical formulation of a dermatological agent, where each container may include a single or multiple dosage amounts of a topical formulation of a dermatological agent. While kit 50 is shown having five hydrogel patch compositions and five containers of topical formulation of dermatological agent, it shall be understood that fewer or more hydrogel patch compositions and/or fewer or more containers of topical formulation of dermatological agent may be included in a kit.

In many embodiments of the subject kits, the hydrogel patch composition(s) and the topical formulation of a dermatological agent are packaged in a kit containment element to make a single, easily handled unit, where the kit containment element, e.g., box or analogous structure, may or may not be an airtight container, e.g., to further preserve the composition of the patches and topical formulation of a dermatological agent until use.

The subject kits also generally include instructions for how to use the hydrogel patch composition to occlude the topical formulation of dermatological agent in order to deliver the dermatological agent to a host. The instructions are generally recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Utility

The subject methods find use in any application in which the topical administration of a dermatological agent to a subject is desired. Generally, such subjects are "mammals" or "mammalian", where these terms are used broadly to describe organisms which are within the class mammalia, including the order carnivore (e.g., dogs and cats), rodentia (e.g., mice, guinea pigs, and rats), and primates (e.g., humans, chimpanzees, and monkeys). In many embodiments, the subject is a human.

In many embodiments, the subject invention finds use in the treatment of a disease condition. By treatment it is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as dermatitis and the like. As such, treatment also includes situations where the pathological condition, or at least symptoms associated therewith, are completely inhibited, e.g., prevented from happening, or stopped, e.g., terminated, such that the host no longer suffers from the pathological condition, or at least the symptoms that characterize the pathological condition. As such, treatment includes both curing and managing a disease condition.

Accordingly, the subject methods may be used to treat a wide variety of disease conditions or disorders as long as the disease disorder is capable of being treated with a topical dermatological agent or at least suspected being treatable with a topical dermatological agent. As noted above, in certain embodiments of the subject invention, a dermatological agent is not employed. The subject methods are particularly well suited for disease conditions that affect the skin and thus may be correctly characterized as skin conditions or dermatological conditions. As used herein, the term "skin condition" and analogous terms are used broadly to refer to any condition of the skin in need of treatment, including those that do not involve inflammation of the skin, e.g., vitiligo. These skin disorders may be the result of a bacterial infection, viral infection, fungal infection, auto-immune response, allergenic response, idiopathic, and the like and may be acute or chronic lasting from a few minutes to a lifetime. As such, the subject methods include any disease condition including those that originate at or are localized to the skin, as well as disease conditions that originate elsewhere in the body and/or are not localized to the skin. In other words, disease conditions that may affect the skin may originate in another organ or system of the body, but may have manifestations or symptoms that affect the skin. Disease conditions that may be treated in accordance with the subject inventions include, but are not limited to: psoriasis, eczema, vitiligo, atopic dermatitis, contact dermatitis, nummular dermatitis, generalized exfoliative dermatitis, stasis dermatitis; perioral dermatitis, morphoea, palmoplantar pustulosis, ichthyosis, keratoderma, warts, porokeratosis, Hailey-Hailey disease, pityriasis rubra pilaris, acanthosis nigricans, rosacea, lupus erythmatosus, Lichen simplex chronicus (neurodermatitis), alopecia, seborrheia, actinic keratosis, corns, pruritis, sun burn, urticaria, localized scratch dermatitis, staphylococcal disorders, ertsipelas, folliculitis, carbuncles, furuncles, erythrasma, candidiasis, dermatophyte infections, scabies, pediculosis, hypertrichosis, lichen planus, etc.

EXPERIMENTAL

The following examples are put forth so as to provide those of ordinary skill in the art with a complete disclosure and description of how to make and use the present invention, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

PRACTICAL EXAMPLES

For each example, erythema, induration and scaling were graded based on a scale of 0-4. Scores reported in each example indicate a combined (total) score of the criteria below (e.g., erythema 3+indulation 2+scaling 4=a total score of 9).

| | Erythema | |
|---|---|---|
| 0 | None | No Erythema |
| 1 | Mild | Faintly Detectable/Pink |
| 2 | Moderate | Red |
| 3 | Severe | Very Red |
| 4 | Very Severe | Extremely |

| | Induration | |
|---|---|---|
| 0 | None | No Elevation |
| 1 | Mild | Slight Elevation |
| 2 | Moderate | Moderate Elevation with Rounded or Sloped Edges to Plaque |
| 3 | Severe | Marked Elevation with Very Hard, Sharp Edges to Plaque |
| 4 | Very Severe | Very Marked Elevation with Very Hard, Sharp Edges to Plaque |

| | Scaling | |
|---|---|---|
| 0 | None | No Scaling |
| 1 | Mild | Fine Scales, Partially Covering Lesions |
| 2 | Moderate | Coarser Scales, Partially Covering Lesions |
| 3 | Severe | Course, Thick Scales; Lesions Covered; rough surface |
| 4 | Very Severe | Course, Very Thick Scales; Lesions Covered; Very Rough Surface |

A. Practical Example 1

Administration of Triamcinolone 0.1% to Treat Psoriasis with and without Occlusion by a Hydrogel Patch Composition Protocol:

Two times a day for a period of two weeks, triamcinolone 0.1% ointment was topically applied to two symmetrical psoriatic lesions on a human host. A subject blank hydrogel patch composition was used to occlude the topically applied triamcinolone 0.1% ointment over one of the lesions while the other topically applied triamcinolone 0.1% ointment was left un-occluded. The hydrogel patch was changed after each triamcinolone 0.1% application. While the duration of the treatment was two weeks, a final evaluation was performed at the end of the fourth week.

Results:

| Subject Number | Scores for Day #1 (occluded/ unoccluded) | Scores for Week #1 (occluded/ unoccluded) | Scores for Week #2 (occluded/ unoccluded) | Scores for Week #3 (occluded/ unoccluded) | Scores for Week #4 (occluded/ unoccluded) |
| --- | --- | --- | --- | --- | --- |
| 1 | 8.5/8.5 | 3.5/8.0 | 2.5/6.0 | no scores determined for this week | 2.5/6.0 |
| 2 | 6.5/6.0 | 3.0/5.5 | 2.0/4.0 | no scores determined for this week | 6.0/7.0 |

Conclusions:

After four weeks, the lesion that had the occluded topical triamcinolone 0.1% ointment showed improved results as compared to the un-occluded lesion.

B. Practical Example 2

Administration of Clobetasol 0.05% to Treat Psoriasis with and without Occlusion by a Hydrogel Patch Composition Protocol:

Two times a day for a period of two weeks, clobetasol 0.05% ointment was topically applied to two symmetrical psoriatic lesions on a human host. A subject blank hydrogel patch composition was used to occlude the topically applied clobetasol 0.05% ointment over one of the lesions while the other topically applied clobetasol 0.05% ointment was left un-occluded. The hydrogel patch was changed after each clobetasol 0.05% application. While the duration of the treatment was two weeks, a final evaluation was performed at the end of the fourth week.

Results:

| Subject | Scores for Day #1 (occluded/ unoccluded) | Scores for Week #1 (occluded/ unoccluded) | Scores for Week #2 (occluded/ unoccluded) | Scores for Week #3 (occluded/ unoccluded) | Scores for Week #4 (occluded/ unoccluded) |
| --- | --- | --- | --- | --- | --- |
| 1 | 5.5/5.5 | 3.5/4.0 | 1.5/1.5 | no scores determined for this week | 1.0/2.5 |

Conclusions:

After four weeks, the lesion that had the occluded topical clobetasol 0.05% ointment showed improved results as compared to the un-occluded lesion.

C. Practical Example 3

Treatment of Psoriasis with a Hydrogel Patch Composition without a Topically Applied Topical Formulation of Dermatological Agent Protocol:

Two times a day for a period of two weeks, a subject blank hydrogel patch composition was topically applied to a psoriatic lesion on a human host. A symmetrical psoriatic lesion on the host was left untreated as a control. While the duration of the treatment was two weeks, a final evaluation was performed at the end of the fourth week.

Results:

| Subject Number | Scores for Day #1 (occluded/ unoccluded) | Scores for Week #1 (occluded/ unoccluded) | Scores for Week #2 (occluded/ unoccluded) | Scores for Week #3 (occluded/ unoccluded) | Scores for Week #4 (occluded/ unoccluded) |
| --- | --- | --- | --- | --- | --- |
| 1 | 6.5/6.5 | 4.5/6.0 | 5.0/7.0 | no scores determined for this week | 5.5/7.0 |
| 2 | 5.0/4.5 | 3.0/5.5 | 2.0/5.0 | no scores determined for this week | 4.5/5.5 |

Conclusions:

After four weeks, the lesion that had the subject blank hydrogel patch composition showed improved results as compared to the control lesion.

It is evident from the above results and discussion that the subject methods provide an improved method of administering a dermatological agent to a host. The above-described invention provides a number of advantages including cost effectiveness, ease of use, and effective and efficient manners of delivering the dermatological agent to the host, as well as improved delivery of the agent through the skin and therefore better patient outcome. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

The invention claimed is:

1. A method of treating a host for a dermatological condition, said method comprising:
    (a) applying a blank hydrogel patch directly to a skin surface being treated for a dermatological condition without the use of a topically applied formulation of a dermatological agent, wherein said hydrogel patch comprises a hydrogel patch composition present on an impermeable support, said hydrogel patch composition comprising water present in an amount of 25% (w/w) or more; and
    (b) maintaining said hydrogel patch on said skin surface for a period of time sufficient to treat said host for said dermatological condition;
    wherein said dermatological condition is chosen from the group consisting of psoriasis, eczema, atopic dermatitis, contact dermatitis, nummular dermatitis, generalized exfoliative dermatitis, stasis dermatitis, perioral dermatitis, and localized scratch dermatitis.

2. The method according to claim 1, wherein said hydrogel patch composition comprises:
    (i) a water-soluble polymer gel;
    (ii) a water retaining agent; and
    (iii) a cross-linking agent.

3. The method according to claim 2, wherein said water-soluble polymer gel comprises at least one of: gelatin, starch, agar, mannan, alginic acid, polyacrylic acid, polyacrylate, dextrin, methylcellulose, sodium methylcellulose, hydroxypropylcellulose, sodium carboxymethylcellulose, cellulose gum, carboxyvinyl polymer, polyvinyl alcohol, polyvinylpyrrolidone, Arabia gum, acacia, tragacanth gum, karaya gum, starch acrylate copolymer, and starch sodium acrylate graft copolymer.

4. The method according to claim 2, wherein said cross-linking agent is chosen from the group consisting of dried aluminum hydroxy gel, dihydroxy aluminum acetate, magnesium aluminometasilicate, aluminum hydroxide, magnesium metasilicate aluminate, synthetic aluminum silicate, calcium hydroxide, aluminum ammonium sulfate, and calcium chloride and combinations thereof.

5. The method according to claim 2, wherein said water retaining agent is selected from the group consisting of glycerin, sorbitol, propylene glycol, diethylene glycol, 1,3-butylene glycol, and ethylene glycol, and combinations thereof.

6. The method according to claim 1, wherein said dermatological condition is atopic dermatitis.

7. A method of treating a host for a dermatological condition, said method consisting essentially of:
    (a) applying a blank hydrogel patch directly to a skin surface being treated for a dermatological condition without the use of a topically applied formulation of a dermatological agent, wherein said hydrogel patch comprises a hydrogel patch composition present on an impermeable support, said hydrogel patch composition comprising:
        (i) a water-soluble polymer gel;
        (ii) water present in an amount of 25% (w/w) or more;
        (iii) a water retaining agent; and
        (iv) a cross-linking agent; and
    (b) maintaining said hydrogel patch on said skin surface for a period of time sufficient to treat said host for said dermatological condition;
        wherein said dermatological condition is chosen from the group consisting of psoriasis, eczema, atopic dermatitis, contact dermatitis, nummular dermatitis, generalized exfoliative dermatitis, stasis dermatitis, perioral dermatitis, and localized scratch dermatitis.

8. The method according to claim 7, wherein said water is present in an amount of 30% (w/w) or more.

9. The method according to claim 7, wherein said water-soluble polymer gel comprises at least one of: gelatin, starch, agar, mannan, alginic acid, polyacrylic acid, polyacrylate, dextrin, methylcellulose, sodium methylcellulose, hydroxypropylcellulose, sodium carboxymethylcellulose, cellulose gum, carboxyvinyl polymer, polyvinyl alcohol, polyvinylpyrrolidone, Arabia gum, acacia, tragacanth gum, karaya gum, starch acrylate copolymer, and starch sodium acrylate graft copolymer.

10. The method according to claim 7, wherein said cross-linking agent is chosen from the group consisting of dried aluminum hydroxy gel, dihydroxy aluminum acetate, magnesium aluminometasilicate, aluminum hydroxide, magnesium metasilicate aluminate, synthetic aluminum silicate, calcium hydroxide, aluminum ammonium sulfate, and calcium chloride and combinations thereof.

11. The method according to claim 7, wherein said water retaining agent is selected from the group consisting of glycerin, sorbitol, propylene glycol, diethylene glycol, 1,3-butylene glycol, and ethylene glycol, and combinations thereof.

12. The method according to claim 7, wherein said dermatological condition is atopic dermatitis.

13. A method of treating a host for atopic dermatitis, said method consisting of:
    (a) applying a blank hydrogel patch directly to a skin surface being treated for a dermatological condition without the use of a topically applied formulation of a dermatological agent, wherein said hydrogel patch comprises a hydrogel patch composition present on an impermeable support, said hydrogel patch composition comprising:
        (i) a water-soluble polymer gel;
        (ii) water present in an amount of 25% (w/w) or more;
        (iii) a water retaining agent; and
        (iv) a cross-linking agent; and (b) maintaining said hydrogel patch on said skin surface for a period of time sufficient to treat said host for said atopic dermatitis.

14. The method according to claim 13, wherein said water is present in an amount ranging from 30% to 50% (w/w).

15. The method according to claim 13, wherein said water-soluble polymer gel comprises at least one of: gelatin, starch, agar, mannan, alginic acid, polyacrylic acid, polyacrylate, dextrin, methylcellulose, sodium methylcellulose, hydroxypropylcellulose, sodium carboxymethylcellulose, cellulose gum, carboxyvinyl polymer, polyvinyl alcohol, polyvinylpyrrolidone, Arabia gum, acacia, tragacanth gum, karaya gum, starch acrylate copolymer, and starch sodium acrylate graft copolymer.

16. The method according to claim 13, wherein said cross-linking agent is chosen from the group consisting of dried aluminum hydroxy gel, dihydroxy aluminum acetate, magnesium aluminometasilicate, aluminum hydroxide, magnesium metasilicate aluminate, synthetic aluminum silicate, calcium hydroxide, aluminum ammonium sulfate, and calcium chloride and combinations thereof.

17. The method according to claim 1, wherein said hydrogel patch consists of said hydrogel patch composition and said impermeable support.

18. The method according to claim 7, wherein said hydrogel patch consists of said hydrogel patch composition and said impermeable support.

19. The method according to claim 13, wherein said hydrogel patch consists of said hydrogel patch composition and said impermeable support.

\* \* \* \* \*